US005789611A

United States Patent [19]
Isoyama et al.

[11] Patent Number: 5,789,611
[45] Date of Patent: Aug. 4, 1998

[54] METHOD FOR THE PREPARATION OF ACRYLOXY-FUNCTIONAL OR METHACRYLOXY-FUNCTIONAL ORGANOSILICON COMPOUNDS

[75] Inventors: Kazuhiro Isoyama; Yokichi Yamamoto, both of Chiba Prefecture, Japan

[73] Assignee: Dow Corning Toray Silicone Co., Ltd., Tokyo, Japan

[21] Appl. No.: 977,292

[22] Filed: Nov. 24, 1997

[30] Foreign Application Priority Data

Nov. 28, 1996 [JP] Japan ............................ 8-335018

[51] Int. Cl.$^6$ ........................................... C07F 7/08
[52] U.S. Cl. ........................ 556/440; 556/438; 556/439
[58] Field of Search ............................ 556/440, 438, 556/439

[56] References Cited

U.S. PATENT DOCUMENTS

| | | | |
|---|---|---|---|
| 3,925,434 | 12/1975 | Chuang | 556/438 |
| 5,103,032 | 4/1992 | Turner et al. | 556/401 |
| 5,145,979 | 9/1992 | Takatsuna et al. | 556/440 |
| 5,262,555 | 11/1993 | Okawa et al. | 556/440 |
| 5,679,821 | 10/1997 | Takei et al. | 556/438 |
| 5,723,643 | 3/1998 | Mikami et al. | 556/440 |

FOREIGN PATENT DOCUMENTS 5-301881  11/1993  Japan.

*Primary Examiner*—Paul F. Shaver
*Attorney, Agent, or Firm*—William F. Boley

[57] ABSTRACT

An method for the synthesis of high-purity (meth)acryloxy-functional organosilicon compounds in which the generation of reaction by-products is inhibited and gelation of the reaction product does not occur comprising an addition reaction between (A) an acrylate ester or methacrylate ester of an aliphatically unsaturated alcohol and
(B) a SiH-functional organosilicon compound in the presence of
(C) a hydrosilylation-reaction catalyst and
(D) a special type of compound such as the zinc salt of 2-mercaptobenzothiazole or zinc dimethyldithiocarbamate.

11 Claims, No Drawings

METHOD FOR THE PREPARATION OF ACRYLOXY-FUNCTIONAL OR METHACRYLOXY-FUNCTIONAL ORGANOSILICON COMPOUNDS

BACKGROUND OF INVENTION

This invention is a method for the preparation of acryloxy-functional or methacryloxy-functional organosilicon compounds. More particularly, this invention is a very efficient method for the preparation of high-purity acryloxy-functional or methacryloxy-functional organosilicon compounds in which the generation of reaction by-products is inhibited and gelation of the reaction product does not occur.

Organosilicon compounds functionalized with the acryloxy or methacryloxy group (hereinafter abbreviated as (meth)acryloxy-functional organosilicon compounds) readily react with radically-polymerizable monomers such as methyl methacrylate and styrene and as a consequence are used as starting materials for copolymers deriving from these monomers and as modifiers for polymers obtained from these monomers.

These (meth)acryloxy-functional organosilicon compounds are prepared by addition-reacting the acrylate ester or methacrylate ester of an aliphatically unsaturated alcohol with a SiH-functional halosilane and subsequently isolating the (meth)acryloxy-functional organosilicon compound from the reaction mixture by distillative purification (refer, for example, to Japanese Patent Application Laid Open (Kokai or Unexamined) Number Hei 5-301881 (301,881/1993)). However, these addition reactions are frequently accompanied by the generation of reaction by-products such as acrylic acid and methacrylic acid. Moreover, since these reaction by-products as well as the (meth)acryloxy-functional compounds are compounds that readily polymerize upon heating, these methods are also often accompanied by polymerization to high molecular weights and gelation during the addition-reaction stage and during the distillation step. As a consequence, the addition reactions in these methods must be run while maintaining the reaction temperature at a level at which thermal polymerization will not occur. This type of temperature control is quite difficult, however, and the reaction products still often undergo polymerization to high molecular weights and gelation.

Japanese Patent Application Laid Open (Kokai or Unexamined) Number Hei 5-186478 (186,478/1993) discloses a method that uses N,N,-dialkylaminomethylenephenol as polymerization inhibitor. This inhibitor has relatively good effects in terms of inhibiting the polymerization of acrylic-functional silane and halosilane, but it is a poison of the platinum catalysts used as addition-reaction catalysts in the synthesis of these silanes by addition reaction as described above. This method thus suffers from the problem of requiring the use of large amounts of platinum catalyst to complete the reaction.

As a result of extensive investigations directed to solving the problems described above, the inventors have discovered that running the subject addition reaction in the presence of a special type of compound inhibits the generation of reaction by-products and prevents gelation during the addition reaction. The present invention was achieved based on this discovery.

In specific terms, the object of the present invention is to provide a high-yield method for the synthesis of high-purity (meth)acryloxy-functional organosilicon compounds in which during the production of these compounds the generation of reaction by-products is inhibited and gelation of the reaction mixture does not occur.

SUMMARY OF INVENTION

The present invention is a method for the preparation of acryloxy-functional or methacryloxy-functional organosilicon compounds comprising effecting an addition reaction between (A) an acrylate ester or methacrylate ester of an aliphatically unsaturated alcohol and (B) a SiH-functional organosilicon compound in the presence of (C) a hydrosilylation-reaction catalyst and (D) a compound described by general formula

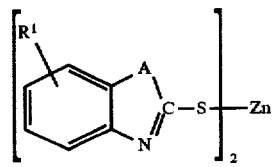

where A is a sulfur atom or NH and $R^1$ is a methyl group or a hydrogen atom or a compound described by general formula

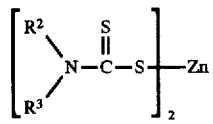

where $R^2$ and $R^3$ are independently selected monovalent hydrocarbon groups. The present method inhibits the generation of reaction by-products and prevents gelation during the addition reaction and very efficiently produces high-purity (meth)acryloxy-functional organosilicon compounds in high yields.

DESCRIPTION OF INVENTION

The present invention is a method for the preparation of acryloxy-functional or methacryloxy-functional organosilicon compounds comprising effecting an addition reaction between (A) an acrylate ester or methacrylate ester of an aliphatically unsaturated alcohol and (B) a SiH-functional organosilicon compound in the presence of (C) a hydrosilylation-reaction catalyst and (D) a compound described by general formula

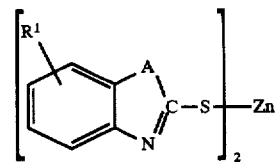

where A is a sulfur atom or NH and $R^1$ is a methyl group or a hydrogen atom or a compound described by general formula

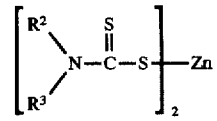

where $R^2$ and $R^3$ are independently selected monovalent hydrocarbon groups.

The acrylate ester of an aliphatically unsaturated alcohol, component (A), used in the present method is exemplified by allyl acrylate, hexenyl acrylate, allyloxyethyl acrylate, and 4-vinylphenyl acrylate. The methacrylate ester of an aliphatically unsaturated alcohol is exemplified by allyl methacrylate, hexenyl methacrylate, allyloxyethyl methacrylate, and 4-vinylphenyl methacrylate.

The SiH-functional organosilicon compound, component (B), used in the present method is not particularly restricted other than that the product afforded by the addition reaction of (B) should have a boiling point in a temperature range capable of distillation. Component (B) is exemplified by trichlorosilane, methyldichlorosilane, dimethylchlorosilane, trimethoxysilane, methyldimethoxysilane, dimethylmethoxysilane, pentamethyldisiloxane, and 1,1,2,2-tetramethyldisiloxane. Component (B) is preferably used at from 0.8 to 1.2 equivalents per equivalent of component (A).

The hydrosilylation-reaction catalyst, component (C), used in the present method is preferably a transition metal catalyst from Group VIII of the Periodic Table, among which platinum catalysts are the most preferred. The instant platinum catalysts are exemplified by the alcohol solutions of chloroplatinic acid, platinum-olefin complexes, and platinum complexes with vinyl-functional siloxane. Component (C) is preferably used at from 0.1 to 200 weight-ppm based on the total quantity of components (A) and (B).

The component (D) used in the present method is the component that characterizes the present invention. This component functions to inhibit the generation of by-products that may be produced during the addition reaction between components (A) and (B) and to prevent the reaction product from polymerizing to high molecular weights and gelling.

Component (D) encompasses compounds described by the following general formula (1)

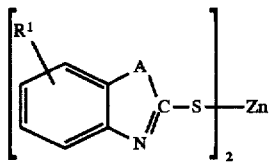

where A is a sulfur atom or NH and $R^1$ is a methyl group or a hydrogen atom and compounds described by general formula (2)

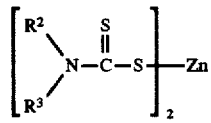

where $R^2$ and $R^3$ are independently selected monovalent hydrocarbon groups. Compound (1) is specifically exemplified by the zinc salt of 2-mercaptobenzothiazole and the zinc salt of 2-mercaptoimidazole. Compounds in which the sulfur atom is selected for A in the preceding formula (1) have the same effect as compounds in which NH is selected for A, and the same is true for the selection of methyl for $R^1$ versus the selection of hydrogen for $R^1$. $R^2$ and $R^3$ in general formula (2) are selected from alkyls such as methyl, ethyl, and butyl and aryl such as phenyl. Compound (2) is specifically exemplified by zinc dimethyldithiocarbamate and zinc diethyldithiocarbamate.

The present method requires the presence of component (D) during the addition reaction between components (A) and (B) under catalysis by component (C). Component (D) is preferably added at from 0.0001 to 1 weight part per 100 weight parts component (A) and particularly preferably at from 0.001 to 0.5 weight part per 100 weight parts component (A).

The present method can be run in the presence or absence of organic solvent. Organic solvents usable for running the method in the presence of organic solvent are exemplified by aromatic hydrocarbons such as benzene, toluene, and xylene; aliphatic hydrocarbons such as hexane and heptane; ethers such as tetrahydrofuran and diethyl ether; ketones such as acetone and methyl ethyl ketone; and esters such as ethyl acetate and butyl acetate.

The present method can be run at room temperature, but is preferably run at temperatures of at least 30° C. in order to obtain good reaction rates. In addition, since the (meth)acryloxy-functional organosilicon compounds readily polymerize and gel at high temperatures, the reaction temperature preferably does not exceed 100° C. and more preferably is in the range of from 30° C. to 90° C.

The reaction mixture afforded by the present method can be purified by distillation directly as obtained upon completion of the reaction. For this distillation the known radical-polymerization inhibitors such as hindered phenol compounds, amine compounds, quinone compounds, and oxygen can be added to the reaction mixture.

The invention will be explained below through working examples, in which % indicates weight %.

EXAMPLE 1

60.0 g (0.48 mol) Allyl methacrylate, 0.04 g chloroplatinic acid/divinyltetramethyldisiloxane complex (this provided 2.7 ppm platinum metal based on the weight of allyl methacrylate), and 0.0033 g ($8.3 \times 10^{-6}$ mol) of the zinc salt of 2-mercaptobenzothiazole were introduced into a 300-mL four-neck flask equipped with a condenser, stirrer, thermometer, and addition funnel. The temperature in the flask was brought to 80° C. and 70.9 g trichlorosilane were gradually added dropwise. After the completion of addition, the reaction was stirred for an additional 1 hour while maintaining the reaction temperature at 80° C. This yielded 119.2 g of a reaction mixture.

The reaction mixture was re-introduced into a four-neck flask; the temperature was brought to 80° C.; and 48.0 g methanol were gradually added dropwise. After the completion of addition, the hydrogen chloride was removed under reduced pressure to give 107.3 g (yield=82%) of a reaction product. Analysis of this reaction product by infrared absorption spectroscopy and nuclear magnetic resonance spectroscopy confirmed it to be γ-methacryloxypropyltrimethoxysilane.

Analysis of the reaction by-product in this reaction product by ion chromatography showed that only 25 weight-ppm methacrylic acid was present in the reaction product.

EXAMPLE 2

60.0 g (0.48 mol) Allyl methacrylate, 0.04 g (2.7 ppm) chloroplatinic acid/divinyltetramethyldisiloxane complex, and 0.0025 g ($8.3 \times 10^{-6}$ mol) zinc dimethyldithiocarbamate were introduced into a 300-mL four-neck flask equipped with a condenser, stirrer, thermometer, and addition funnel. The temperature in the flask was brought to 80° C. and 70.9 g (0.52 mol) trichlorosilane were gradually added dropwise. After the completion of addition, the reaction was stirred for an additional 1 hour while maintaining the reaction temperature at 80° C. This yielded 121.0 g of a reaction mixture.

The reaction mixture was re-introduced into a four-neck flask; the temperature was brought to 80° C.; and 48.9 g methanol were gradually added dropwise. After the completion of addition, the hydrogen chloride was removed under reduced pressure to give 109.0 g (yield=83%) of a reaction product. Analysis of this reaction product by infrared absorption spectroscopy and nuclear magnetic resonance spectroscopy confirmed it to be γ-methacryloxypropyltrimethoxysilane.

Analysis of the reaction by-product in this reaction product by ion chromatography showed that only 25 weight-ppm methacrylic acid was present in the reaction product.

Comparative Example 1

An addition reaction was run as in Example 1, but in this case without the addition of the zinc salt of 2-mercaptobenzothiazole that was used in Example 1. 105.8 g (yield=81%) Reaction product was obtained. Analysis of this reaction product by infrared absorption spectroscopy and nuclear magnetic resonance spectroscopy confirmed it to be γ-methacryloxypropyltrimethoxysilane.

Analysis of the reaction by-product in this reaction product by ion chromatography showed that 1,105 weight-ppm methacrylic acid was present in the reaction product.

Comparative Example 2

An addition reaction was run as in Example 2, but in this case without the addition of the zinc dimethyldithiocarbamate that was used in Example 2. In this case, the reaction product lost fluidity and converted to a gel 30 minutes after the start of the dropwise addition of the trichlorosilane.

We claim:

1. A method for preparation of acryloxy-functional or methacryloxy-functional organosilicon compounds comprising effecting an addition reaction between
    (A) an acrylate ester or methacrylate ester of an aliphatically unsaturated alcohol and
    (B) a SiH-functional organosilicon compound in the presence of
    (C) a hydrosilylation-reaction catalyst and
    (D) a compound described by general formula

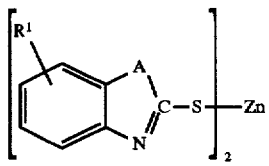

where A is a sulfur atom or NH and $R^1$ is a methyl group or a hydrogen atom or a compound described by general formula

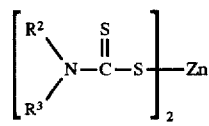

where $R^2$ and $R^3$ are independently selected monovalent hydrocarbon groups.

2. The method according to claim 1, where the quantity of component (D) is from 0.0001 to 1 weight part per 100 weight parts of component (A).

3. The method according to claim 1, where the quantity of component (D) is from 0.001 to 0.5 weight part per 100 weight parts of component (A).

4. The method according to claim 1, where component (D) is selected from the group consisting of zinc salt of 2-mercaptobenzothiazole and zinc salt of 2-mercaptoimidazole.

5. The method according to claim 1, where component (D) is selected from the group consisting of zinc dimethyldithiocarbamate and zinc diethyldithiocarbamate.

6. The method according to claim 1, where component (A) is allyl methacrylate, component (B) is trichlorosilane, component (C) comprises a chloroplatinic acid/divinyltetramethyldisiloxane complex, and component (D) is zinc salt of 2-mercaptobenzothiazole.

7. The method according to claim 1, where component (A) is allyl methacrylate, component (B) is trichlorosilane, component (C) comprises a chloroplatinic acid/divinyltetramethyldisiloxane complex, and component (D) is zinc dimethyldithiocarbamate.

8. The method according to claim 1, where component (A) is allyl methacrylate.

9. The method according to claim 1, where component (B) is trichlorosilane.

10. The method according to claim 1, where component (A) is allyl methacrylate and component (B) is trichlorosilane.

11. The method according to claim 1, where the addition reaction is effected at a temperature within a range of 30° C. to 90° C.

* * * * *